United States Patent [19]

de Roose

[11] Patent Number: Plant 6,619

[45] Date of Patent: Feb. 21, 1989

[54] *VRIESIA POELMANII* PLANT NAMED WHITE LINE

[75] Inventor: Albert de Roose, Evergem, Belgium

[73] Assignee: J. J. Henny Bos, Pijnacker, Netherlands

[21] Appl. No.: 96,540

[22] Filed: Sep. 15, 1987

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

*Vriesia poelmanii* White Line is characterized by its variegated foliage comprised of a yellow to light green stripe running centrally longitudinally of the leaf, with darker green areas extending from the margins of the stripe to the edges of the leaves. The variegated foliage, together with the bright red bracts and yellow flower color combine to achieve a very striking and colorful cultivar.

2 Drawing Sheets

The present invention relates to a new cultivar of the species *Poelmanii* of the genus Vriesia of the family Bromeliaceae. The species *Vriesia poelmanii* is a very showy plant comprised of normally green leaves growing in rosette form, at the center of which are generally spike-shaped bracts bearing tubular-shaped flowers. The species is cultivated in great quantities.

The new cultivar was discovered by applicant in Evergem, Belgium, in 1960 in a cultivated area growing among plants of an unnamed variety of the species *Vriesia poelmanii* in cultivation at that time. The new cultivar was recognized immediately due to its variegated leaves, having a generally creamy yellow to light green stripe running longitudinally down the center of the leaf. The parent cultivar, like other plants of the same species growing nearby, had leaves which were of a uniform, generally dark green color.

The newly discovered mutation flowered for the first time in 1962, and subsequent asexual propagation of the new cultivar by applicant in Evergem, Belgium has clearly demonstrated that the new cultivar propagates true to type through successive generations. Asexual reproduction has heretofore been exclusively performed by taking sideshoots which are formed from the leaf axils after the plant has flowered.

The new cultivar is similar in many respects to the characteristics of the parent cultivar, for example, compact growth habit, relatively quick growing, very good main leaf color, bract color and formation, and flowers which are long-lasting. As above noted, the new cultivar is readily distinguishable from its parent by the yellow to light green stripe which runs longitudinally of the leaf in approximately the center thereof.

White Line has not been observed under all possible environmental conditions. The phenotype may vary with variations in environment such as temperature, light intensity and day length. The following observations, measurements and comparisons describe plants grown in De Lier, the Netherlands under greenhouse conditions which approximate those used in commercial practice.

The accompanying photographic drawings show typical inflorescence and foliage characteristics of White Line. Sheet 1 is a top perspective view of the entire plant, showing the striped variegated leaves and the vivid and contrasting bract formation. Sheet 2 comprises an enlarged showing of the bract formation, with a flower extending above the edge of one of the bracts.

PLANT

The diameter of a fully grown plant on White Line is approximately 60 centimeters. The heighth of the plant, including flower bracts and flowers, is approximately 44 centimeters, with the height of the foliage only being approximately 25 centimeters.

Leaves

The leaves are variegated, with a light yellow-green stripe of color R.H.S. 115D extending longitudinally midway of the leaf. The main green color to either side of the stripe and extending to the non-serrated edges of the leaves is R.H.S. 137A, the same color appearing uniformly throughout the leaves of the parent cultivar. The yellow to light green stripe is approximately 1–2 centimeters wide on fully grown leaves. Longitudinally extending striations of the main green color will occasionally appear in the stripe, although not sufficient to detract from the striking variegation of the leaves.

BRACTS

The bracts are generally spike-shaped, collectively forming a main sword which can extend from the center of a fully grown plant approximately 36–40 centimeters, well above the variegated leaves and forming a very striking contrast with the leaves. There are at least two ramifications present, each of which is approximately 13–15 centimeters in length. The bracts are approximately 3–4 centimeters wide. The color of the bracts is a bright and vivid R.H.S. 46B.

FLOWERS

The flowers are generally tubular-shaped, R.H.S. 9B in color. The flowers are about 3 centimeters long, of which 2.5 cm is disposed within the bract. The length of the stamen is approximately 1 centimeter above the flower and is of the same color. The pistil rises about one-half centimeter above the stamen. It will be noted from one closeup photograph that there is a very sharp and pleasant contrast between the bract and flower colors. This together with the variegated foliage produces a plant of unusual beauty.

I claim:

1. The *Vriesia poelmanii* plant named White Line, as illustrated and described.

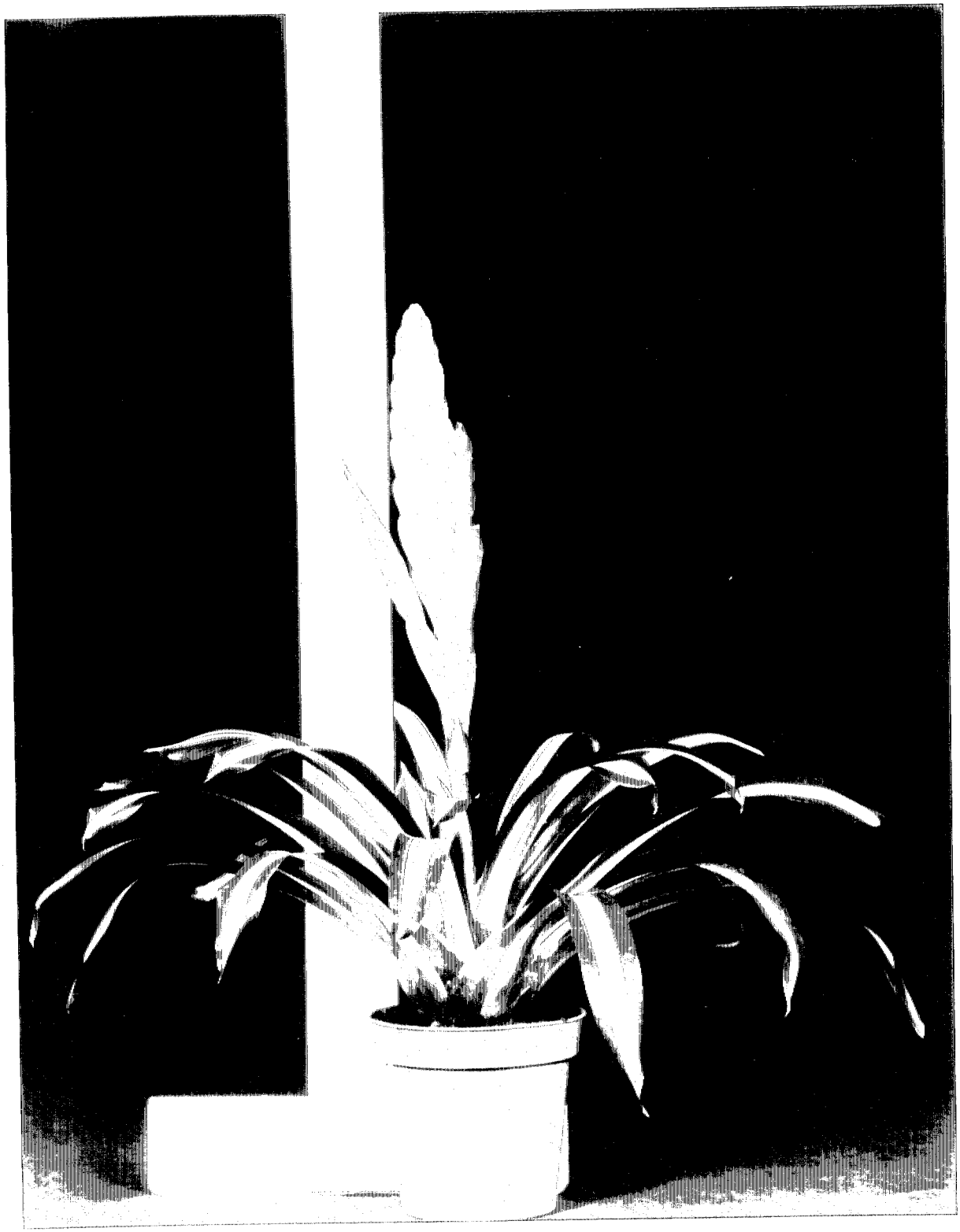

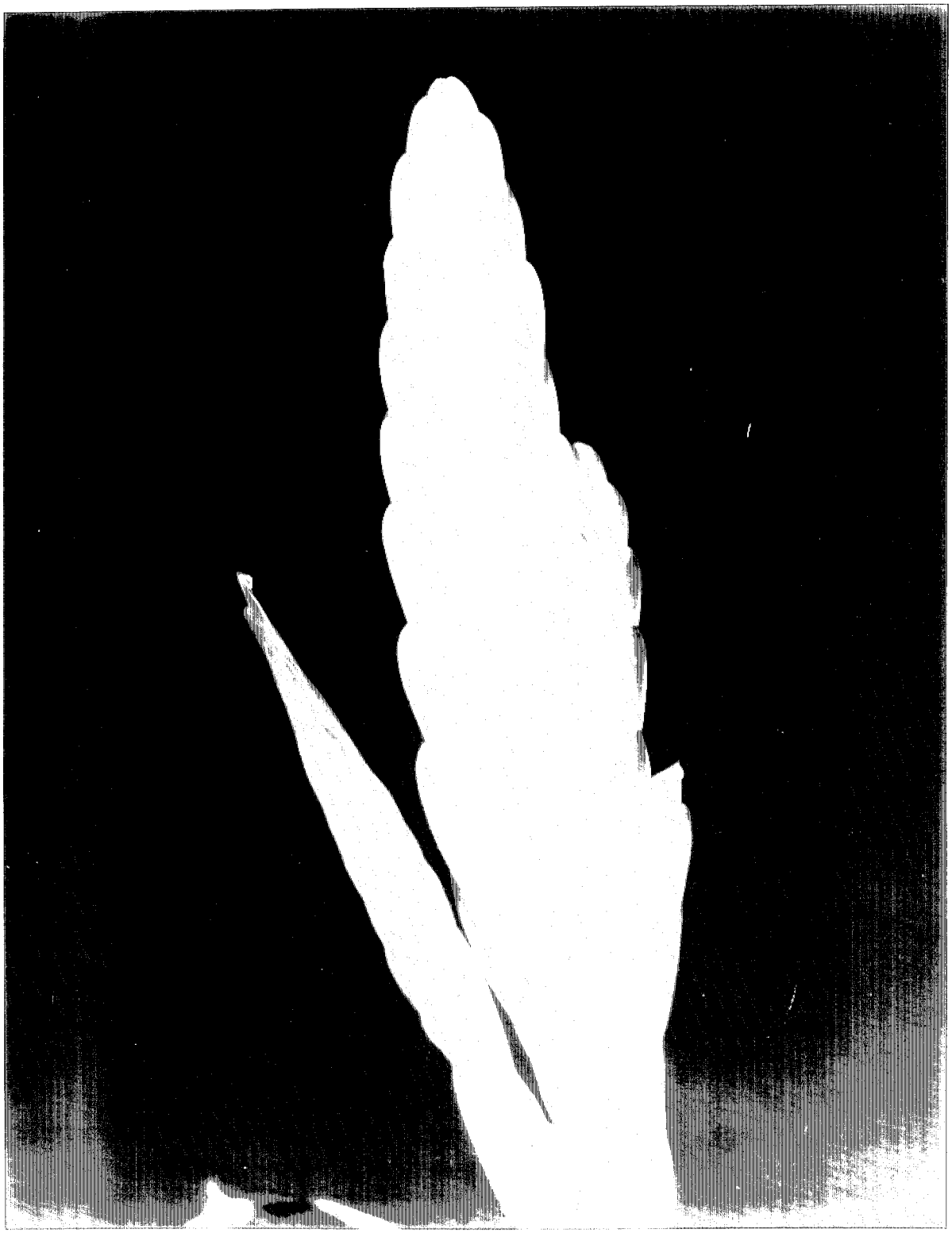

* * * * *